US009687612B2

(12) United States Patent
Avery et al.

(10) Patent No.: US 9,687,612 B2
(45) Date of Patent: Jun. 27, 2017

(54) DOSE SETTING MECHANISM AND DRUG DELIVERY DEVICE

(75) Inventors: Richard James Vincent Avery, Gloucestershire (GB); Paul Richard Draper, Worcestershire (GB); Aled Meredydd James, West Midlands (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1066 days.

(21) Appl. No.: 13/881,806

(22) PCT Filed: Nov. 8, 2011

(86) PCT No.: PCT/EP2011/069582
§ 371 (c)(1),
(2), (4) Date: Apr. 26, 2013

(87) PCT Pub. No.: WO2012/062717
PCT Pub. Date: May 18, 2012

(65) Prior Publication Data
US 2013/0218079 A1    Aug. 22, 2013

Related U.S. Application Data

(60) Provisional application No. 61/411,012, filed on Nov. 8, 2010.

(30) Foreign Application Priority Data

Dec. 13, 2010    (EP) .................................... 10194728

(51) Int. Cl.
*A61M 5/315*    (2006.01)
*A61M 5/24*    (2006.01)

(52) U.S. Cl.
CPC .......... *A61M 5/31538* (2013.01); *A61M 5/24* (2013.01); *A61M 5/3155* (2013.01);
(Continued)

(58) Field of Classification Search
CPC ............ A61M 5/31535; A61M 5/3155; A61M 5/31528; A61M 2205/60;
(Continued)

(56) References Cited

U.S. PATENT DOCUMENTS 6,648,859 B2    11/2003    Bitdinger et al.
6,936,032 B1    8/2005    Bush, Jr. et al.
(Continued)

FOREIGN PATENT DOCUMENTS

EP    0897728 A1    2/1999
JP    H07-500039    1/1995
(Continued)

OTHER PUBLICATIONS

International Search Report and Written Opinion for Int. App. No. PCT/EP2011/069582, mailed Apr. 3, 2012.
(Continued)

*Primary Examiner* — Bhisma Mehta
*Assistant Examiner* — Nilay Shah
(74) *Attorney, Agent, or Firm* — McDonnell Boehnen Hulbert & Berghoff LLP

(57) ABSTRACT

A dose setting mechanism that prevents dispensing of a drug when an incorrect cartridge assembly is attached to the dose setting mechanism. Dispense of a drug may be allowed by preventing rotation of a spindle nut of a drug delivery device, and dispense of a drug may be prevented by not preventing rotation of the spindle nut. Preventing dispense of a drug may be accomplished by preventing rotation of the spindle when an incorrect cartridge assembly is inserted. Preventing dispense of a drug may be accomplished by preventing the spindle from applying an axial force on the cartridge when an incorrect cartridge assembly is inserted.

13 Claims, 8 Drawing Sheets

(52) U.S. Cl.
CPC .... *A61M 5/31535* (2013.01); *A61M 5/31543* (2013.01); *A61M 5/31585* (2013.01); *A61M 5/31528* (2013.01); *A61M 2205/6045* (2013.01)

(58) Field of Classification Search
CPC ............ A61M 2205/6045; A61M 5/20; A61M 5/31566; A61M 5/31565; A61M 5/31576; A61M 5/31571; A61M 5/31583; A61M 5/31586; A61M 5/31543
See application file for complete search history.

(56) References Cited

U.S. PATENT DOCUMENTS

| | | | |
|---|---|---|---|
| 2009/0227955 A1 | 9/2009 | Hirschel et al. | |
| 2009/0275914 A1* | 11/2009 | Harms | A61M 5/31551 604/506 |
| 2009/0275916 A1 | 11/2009 | Harms et al. | |
| 2010/0114025 A1* | 5/2010 | Moller | A61M 5/20 604/135 |

FOREIGN PATENT DOCUMENTS

| | | |
|---|---|---|
| JP | 2004-500904 | 1/2004 |
| WO | 93/07922 | 4/1993 |
| WO | 9307922 A1 | 4/1993 |
| WO | 2008/019514 | 2/2008 |
| WO | 2008019514 A1 | 2/2008 |
| WO | 2008/074897 | 6/2008 |
| WO | 2008074897 A1 | 6/2008 |
| WO | 2009/132781 | 11/2009 |
| WO | 2009132781 A1 | 11/2009 |
| WO | 2010/006870 | 1/2010 |
| WO | 2010006870 A1 | 1/2010 |

OTHER PUBLICATIONS

Japanese Office Action for JP App. No. 2013-537161, dated Sep. 15, 2015.
Chinese Search Report for CN App. No. 2011800642402, dated Apr. 24, 2015.
Form PCT/ISA/220, Notification of Transmittal of the International Search Report and the Written Opinion of the International Searching Authority, or the Declaration, dated Apr. 3, 2012.
English Translation of the Notification of Reasons for Refusal issued in Japanese Patent Application No. 2013-537161 dated Sep. 15, 2015.
International Search Report for Int. App. No. PCT/EP2011/069582, completed Mar. 27, 2012.

* cited by examiner

DOSE SETTING MECHANISM AND DRUG DELIVERY DEVICE

CROSS REFERENCE TO RELATED APPLICATIONS

The present application is a U.S. National Phase Application pursuant to 35 U.S.C. §371 of International Application No. PCT/EP2011/069582 filed Nov. 8, 2011, which claims priority to U.S. Provisional Patent Application No. 61/411,012 filed Nov. 8, 2010 and European Patent Application No. 10194728.1 filed on Dec. 13, 2010. The entire disclosure contents of these applications are herewith incorporated by reference into the present application.

FIELD OF DISCLOSURE

The present patent application is generally directed to reservoirs, particularly reservoirs containing a medicament. More particularly, the present application is generally directed to a drug delivery device that prevents dispensing of a dose when an incorrect reservoir is attached, so as to prevent unwanted reservoir cross use. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user simply loads a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g., 3 ml cartridges). Therefore, there may be a variety of cartridges supplied by a number of different suppliers and containing a different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and design an injection device that only accepts or works with the dedication or coded features provided on or with the cartridge so as to prevent unwanted cartridge cross use. Similarly, there is also a general need for a dedicated cartridge that allows the medical delivery device to be used with only an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products.

SUMMARY

It is an object of the invention to facilitate the use of a correct cartridge in conjunction with a dose setting mechanism.

This object is achieved with the dose setting mechanism and the drug delivery device according to the appended claims. Embodiments emerge from the dependent claims.

In the following, the term "distal end" designates that end of a dose setting mechanism, a drug delivery system or a component thereof which is or is to be arranged closest to a dispensing end, and the term "proximal end" designates that end which is or is to be arranged furthest away from the dispensing end of the device.

The term "drug", "medicament" or "medication" as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(w-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

```
H-(Lys)4-des Pro36, des Pro37
Exendin-4(1-39)-NH2,

H-(Lys)5-des Pro36, des Pro37
Exendin-4(1-39)-NH2, des Pro36 [Asp28]
Exendin-4(1-39), des Pro36 [IsoAsp28]
Exendin-4(1-39), des Pro36 [Met(O)14, Asp28]
Exendin-4(1-39), des Pro36 [Met(O)14, IsoAsp28]
Exendin-4(1-39), des Pro36 [Trp(O2)25, Asp28]
Exendin-4(1-39), des Pro36 [Trp(O2)25, IsoAsp28]
Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39);
or des Pro36 [Asp28]
Exendin-4(1-39), des Pro36 [IsoAsp28]
Exendin-4(1-39), des Pro36 [Met(O)14, Asp28]
Exendin-4(1-39), des Pro36 [Met(O)14, IsoAsp28]
Exendin-4(1-39), des Pro36 [Trp(O2)25, Asp28]
Exendin-4(1-39), des Pro36 [Trp(O2)25, IsoAsp28]
Exendin-4(1-39), des Pro36 [Met(O)14 Trp(O2)25, Asp28]
Exendin-4(1-39), des Pro36 [Met(O)14 Trp(O2)25, IsoAsp28]
Exendin-4(1-39),
``` wherein the group -Lys6-NH2 may be bound to the C-terminus of the Exendin-4 derivative;

or an Exendin-4 derivative of the sequence

```
H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2,
```

-continued

```
H-(Lys)6-des Pro36 [Trp(O2)25, Asp28] Exendin-4(1-39)-Lys6-NH2,

H-des Asp28 Pro36, Pro37, Pro38 [Trp(O2)25] Exendin-4(1-39)-NH2,

H-(Lys)6-des Pro36, Pro37, Pro38 [Trp(O2)25, Asp28] Exendin-4(1-39)-NH2,

H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28]
Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28]
Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28]
Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28]
Exendin-4(S1-39)-(Lys)6-NH2, H-Asn-(Glu)5-des Pro36, Pro37, Pro38 [Met(O)14, Trp(O2)25, Asp28]
Exendin-4(1-39)-(Lys)6-NH2;
``` or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The dose setting mechanism comprises a spindle and a coding feature, wherein inserting a cartridge assembly having a corresponding coding feature in the dose setting mechanism allows to dispense a dose by means of the spindle, and wherein inserting a cartridge assembly that does not have the corresponding coding feature in the dose setting mechanism prevents dispensing a dose.

According to an exemplary arrangement, a dose setting mechanism may include a spindle, a spindle nut, and a coding feature. The spindle nut is engaged with the spindle. When a correct cartridge assembly is inserted in the dose setting mechanism, the coding feature interacts with a corresponding coding feature of the cartridge holder to prevent the spindle nut from rotating. However, when an incorrect cartridge assembly that does not have the corresponding coding feature is inserted into the dose setting mechanism, the spindle nut is free to rotate, and the free rotation of the spindle nut prevents axial movement of the spindle. The spindle nut comprises protrusions, teeth or cams facing the cartridge assembly and preventing the spindle nut from rotation when a cartridge assembly having a corresponding coding feature is inserted.

In another arrangement, a dose setting mechanism includes a main body, a spindle, and a locking disc. An inner edge of the main body comprises at least one main-body spline feature. The spindle has at least one spindle spline feature disposed on an outer edge of the spindle. Further, the locking disc comprises (i) at least one indentation disposed on an inner edge of the locking disc and (ii) at least one indentation disposed on an outer edge of the locking disc. The at least one indentation disposed on an inner edge of the locking disc is configured to engage with the at least one spindle spline feature, and the at least one indentation disposed on the outer edge is configured to engage with the at least one main-body spline feature. Prior to a cartridge assembly being inserted in the dose setting mechanism, the locking disc is engaged with the spindle. When a correct cartridge assembly coded to the dose setting mechanism is inserted in the dose setting mechanism, the cartridge assembly displaces the locking disc in a proximal direction, wherein the displacement disengages the locking disc from the spindle. However, when an incorrect cartridge assembly not coded to the dose setting mechanism is inserted in the dose setting mechanism, the locking disc remains engaged with the spindle.

In yet another arrangement, a dose setting mechanism includes a spindle and a dispensing lock feature. The spindle has a plunger disposed on a distal end of the spindle. Further, the dispensing lock feature is capable of a locked position and an unlocked position. When a correct cartridge assembly is inserted into the dose setting mechanism, the dispensing lock feature is forced into the unlocked position, thereby allowing the plunger to pass beyond the dispensing lock feature. However, when an incorrect cartridge assembly is inserted into the dose setting mechanism, the dispensing lock feature remains in the locked position, and the dispensing lock feature in the locked position prevents the plunger from advancing beyond the dispensing lock.

In a first aspect a dose setting mechanism comprises a spindle, a spindle nut, wherein the spindle nut is engaged with the spindle, and a coding feature, wherein, when a correct cartridge assembly is inserted in the dose setting mechanism, the coding feature interacts with a corresponding coding feature of the cartridge holder to prevent the spindle nut from rotating, and wherein, when an incorrect cartridge assembly that does not have the corresponding coding feature is inserted in the dose setting mechanism, the spindle nut is free to rotate, wherein free rotation of the spindle nut prevents the spindle nut from applying an axial force on the cartridge.

In an example embodiment of the dose setting mechanism, the spindle has a first helical groove extending along an outer surface of the spindle, and the spindle nut has a second helical groove extending along an internal surface of the spindle nut, the first helical groove being engaged with the second helical groove.

In a further example embodiment of the dose setting mechanism, preventing the spindle nut from rotating allows for dispensing of a dose.

In a further example embodiment of the dose setting mechanism, preventing the spindle nut from applying an axial force on the cartridge prevents dispensing of a dose.

In a further example embodiment of the dose setting mechanism, the coding feature is a coding feature disposed on the spindle nut.

In a further example embodiment of the dose setting mechanism, during the interaction with the corresponding coding feature of the cartridge assembly, the coding feature and the corresponding coding feature mesh together.

In a further example embodiment of the dose setting mechanism, the coding feature comprises a plurality of protrusions.

In a further example embodiment of the dose setting mechanism, the corresponding coding features comprise a plurality of corresponding protrusions, and during the interaction the corresponding protrusions mesh with the protrusions.

In a further example embodiment of the dose setting mechanism, the dose setting mechanism comprises a lock nut, and the coding feature is disposed on the lock nut.

In a further example embodiment of the dose setting mechanism, when the correct drug cartridge is inserted, the coding feature and the corresponding coding feature mesh during an initial fastening action, and thereafter the lock nut and cartridge assembly travel axially, and the lock nut engages with the spindle nut.

A further example embodiment of the dose setting mechanism further comprises a spring in communication with the lock nut, the spring preventing the lock nut from engaging with the spindle nut when a cartridge assembly is not inserted.

In a further example embodiment of the dose setting mechanism, the coding feature comprises a plurality of protrusions.

In a further example embodiment of the dose setting mechanism, the plurality of protrusions on the lock nut mesh with the corresponding coding feature of the cartridge assembly.

In a further example embodiment of the dose setting mechanism, the dose setting mechanism comprises a distal lock nut, and the coding feature is located on the distal lock nut, the dose setting mechanism further comprising a proximal lock nut, wherein the distal lock nut is fixed axially to the proximal lock nut, and at least one spline disposed on an inner wall of a housing of the dose setting mechanism, wherein the at least one spline prevents the proximal lock nut from rotating and allows the proximal lock nut to move axially.

A further example embodiment of the dose setting mechanism further comprises a spring, the spring preventing the proximal lock nut from engaging with the spindle nut when a cartridge assembly is not inserted.

In a further example embodiment of the dose setting mechanism, the coding feature comprises at least one of protrusion and an indentation.

In a further example embodiment of the dose setting mechanism, the corresponding coding feature is located on the cartridge assembly.

In a further example embodiment of the dose setting mechanism, the distal lock nut can rotate relative to the proximal lock nut.

A further example embodiment of the dose setting mechanism further comprises a lock nut, the coding feature being disposed on the lock nut and the corresponding coding feature being disposed on a collar of the cartridge assembly.

In a further example embodiment of the dose setting mechanism, the coding feature comprises at least one cam feature, and the corresponding coding feature comprises at least one corresponding cam feature.

In a further example embodiment of the dose setting mechanism, the cam features interact with one another during a rotational part of a fastening operation.

In a further example embodiment of the dose setting mechanism, the interaction of the cam features drive the lock nut axially to mesh with the spindle nut and prevent rotation of the spindle nut.

In a further example embodiment of the dose setting mechanism, the dose setting mechanism comprises a lock nut, and the at least one cam is disposed on the lock nut.

In a further example embodiment of the dose setting mechanism, the lock nut further comprises features for interacting with the spindle nut.

In a further example embodiment of the dose setting mechanism, the at least one cam feature is disposed on the spindle nut, the spindle nut further including at least one tooth feature, wherein when the at least cam feature interacts with the at least one corresponding cam feature, the at least one tooth feature prevents the spindle nut from rotating.

In a further example embodiment of the dose setting mechanism, the at least one cam feature comprises a first cam feature and a second cam feature, the first and second cam being different sizes to indicate the particular drug contained in the cartridge.

In a further example embodiment of the dose setting mechanism, the cartridge assembly only fits in the dose setting mechanism in one orientation.

In a second aspect a dose setting mechanism for use with a cartridge assembly which is intended for use with the dose setting mechanism comprises a main body, wherein an inner edge of the main body comprises at least one main-body spline feature, a spindle, which has at least one spindle spline feature disposed on an outer edge of the spindle, a locking disc, which comprises at least one indentation disposed on an inner edge of the locking disc and at least one indentation disposed on an outer edge of the locking disc, the at least one indentation disposed on an inner edge of the locking disc being configured to engage with the at least one spindle spline feature, and the at least one indentation disposed on the outer edge being configured to engage with the at least one main-body spline feature, wherein, prior to a cartridge assembly being inserted in the dose setting mechanism, the locking disc is engaged with the spindle, wherein, when a correct cartridge assembly coded to the dose setting mechanism is inserted in the dose setting mechanism, the cartridge assembly displaces the locking disc in a proximal direction, wherein the displacement disengages the locking disc from the spindle, and wherein, when an incorrect cartridge assembly not coded to the dose setting mechanism is inserted in the dose setting mechanism, the locking disc remains engaged with the spindle.

In an example embodiment of the dose setting mechanism, the dose setting mechanism further comprises a spindle lock nut, the spindle lock nut being engaged with the spindle.

In a further example embodiment of the dose setting mechanism, the dose setting mechanism further comprises a spring, the spring biasing the locking disc to engage with the spindle when a cartridge assembly is not inserted.

In a further example embodiment of the dose setting mechanism, a correct cartridge assembly comprises a coding feature, which interacts with the locking disc to disengage the locking disc from the spindle.

In a further example embodiment of the dose setting mechanism, the coding feature is due to a position of an end face of the cartridge assembly.

In a third aspect, a dose setting mechanism for use with a cartridge assembly which is intended for use with the dose setting mechanism comprises a main body, wherein an inner edge of the main body comprises at least one main-body spline feature, a spindle, which has at least one spindle spline feature disposed on an outer edge of the spindle a locking disc, which comprises at least one indentation disposed on an inner edge of the locking disc and at least one indentation disposed on an outer edge of the locking disc, wherein the at least one indentation disposed on an inner edge of the locking disc is configured to engage with the at least one spindle spline feature, and wherein the at least one indentation disposed on the outer edge is configured to engage with the at least one main-body spline feature, wherein, prior to a cartridge assembly being inserted in the dose setting mechanism, the locking disc is engaged with the at least one main-body spline feature, wherein, when a correct cartridge assembly coded to the dose setting mechanism is inserted in the dose setting mechanism, the cartridge assembly displaces the locking disc in a proximal direction, wherein the displacement disengages the locking disc from the at least one main-body spline feature, and wherein, when an incorrect cartridge assembly not coded to the dose setting mechanism is inserted in the dose setting mechanism, the locking disc remains engaged with the at least one main-body spline feature.

In a fourth aspect a dose setting mechanism comprises a spindle which has a plunger disposed on a distal end of the spindle and a dispensing lock feature, which is capable of a locked position and an unlocked position, wherein when a correct cartridge assembly is inserted into the dose setting mechanism, the dispensing lock feature is forced into the unlocked position, thereby allowing the plunger to pass beyond the dispensing lock feature, and wherein when an incorrect cartridge assembly is inserted into the dose setting mechanism, the dispensing lock feature remains in the locked position, and wherein the dispensing lock feature in the locked position prevents the plunger from advancing beyond the dispensing lock.

In an example embodiment of the dose setting mechanism, the dispensing lock feature comprises at least one arm.

In a further example embodiment of the dose setting mechanism, the at least one arm is a plurality of arms.

In a further example embodiment of the dose setting mechanism, the plurality of arms comprises between 2-6 arms.

In a further example embodiment of the dose setting mechanism, in the locked position the at least one arm is directed inward relative to an outer housing of the dose setting mechanism.

In a further example embodiment of the dose setting mechanism, in the unlocked position the at least one arm is directed in a direction generally parallel to an outer housing of the dose setting mechanism.

In a further example embodiment of the dose setting mechanism, a main body of the dispensing lock feature is disposed on an inner wall of the dose setting mechanism.

In a further example embodiment of the dose setting mechanism, the dispensing lock feature comprises a split ring.

In a further example embodiment of the dose setting mechanism, an inner body of the drug delivery device comprises an angled surface, wherein an outer edge of the split ring in the unlocked position the split ring abuts the angled surface, and wherein in the locked position at least a portion of the split ring is above the angled surface.

In a further example embodiment of the dose setting mechanism, the split ring is a generally circular ring shaped object comprising a split.

In a further example embodiment of the dose setting mechanism, the dispensing lock feature can be reset to the locked position after the correct cartridge assembly is removed from the drug delivery device.

In a further example embodiment of the dose setting mechanism, the split ring in the locked position has a diameter smaller than that of the plunger.

In a fifth aspect a drug delivery device comprises a dose setting mechanism, a plunger; and a dispense lock, wherein the dispense lock is deactivated when a correct cartridge is fastened to the device and when axial coding features on the cartridge and dispense lock mesh together.

In a sixth aspect a drug delivery device comprises a dose setting mechanism, a plunger, a spindle, and a locking element engaged with the spindle, wherein when a correct cartridge assembly is fastened to the drug delivery device, the locking disc prevents the spindle from rotating.

In a seventh aspect a drug delivery device comprises a dose setting mechanism, a plunger, a spindle, and a dispensing lock feature, wherein when a correct cartridge assembly is fastened to the drug delivery device, the dispensing lock feature prevents the spindle from advancing in an axial direction.

A drug delivery device may comprise a dose setting mechanism according to any of the embodiments disclosed herein.

The scope of the invention is defined by the content of the claims. The invention is not limited to specific embodiments but comprises any combination of elements of different embodiments. Moreover, the invention comprises any combination of claims and any combination of features disclosed by the claims.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1A:
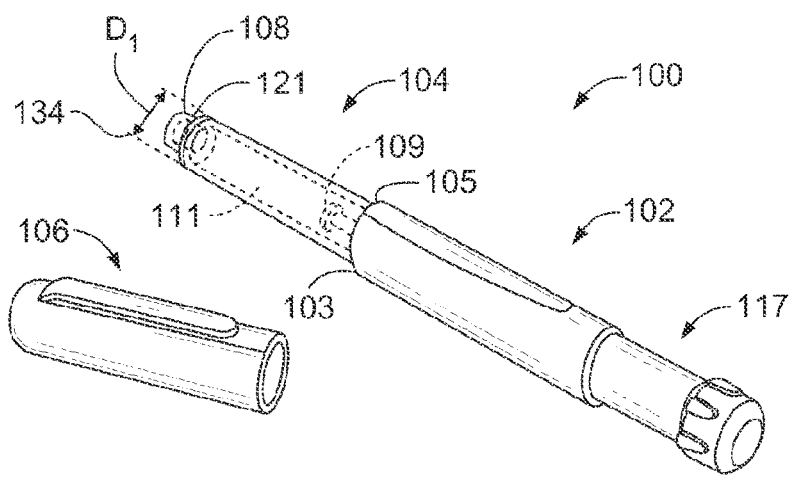
FIG. 1a illustrates an exemplary pen type drug delivery device.

Referring to FIG. 1a, there is shown a drug delivery device 100 in the form of a pen type syringe that may be used with the coding system. This drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The dose setting mechanism 102 may comprise a spindle 109, such as a threaded spindle that rotates when a dose is injected.

To inject a previously set dose, a double ended needle assembly is attached to a distal end 108 of the cartridge holder 104. Preferably, the distal end 108 of the cartridge holder 104 comprises a thread 121 (or other suitable connecting mechanism such as a snap lock, snap fit, form fit, or bayonet lock mechanism) so that the needle assembly may be removably attached to the distal end 108 of the cartridge holder 104. When the drug delivery device 100 is not in use, the removable cap 106 can be releasably retained over the cartridge holder 104.

In one design for the drug delivery device 100, the spindle 108 may comprise two helical grooves of different pitches, one of which is threaded to a nut, and the other threaded to a part of the dispensing mechanism. The nut, which is threaded to the spindle 108, has limited axial travel relative to the drug delivery device 100. Depending on the mode of operation of the dose setting member 102, the nut may or may not rotate relative to the pen body.

To dispense a dose of medicament from the cartridge, the nut must be prevented from rotating. A distal movement of the dispensing mechanism then causes the spindle to advance and rotate. One groove rotates in the dispensing mechanism, and the other groove rotates inside the nut, the difference in thread pitches providing a mechanical advantage.

To reset the spindle before changing to a new cartridge, the nut must be free to rotate. A proximal force applied on the spindle then causes the spindle to retract in the proximal direction. One groove contacts the nut and the other groove contacts the dispensing mechanism, causing rotation of the spindle. Because the groove pitches are different, the nut rotates relative to the pen body.

Although not described, the coding system may apply to other dispensing mechanisms, for example one where the spindle only has one groove and the nut is keyed to it by axial splines, or another where the spindle is a rack driven by a pinion.

Figure 1B:
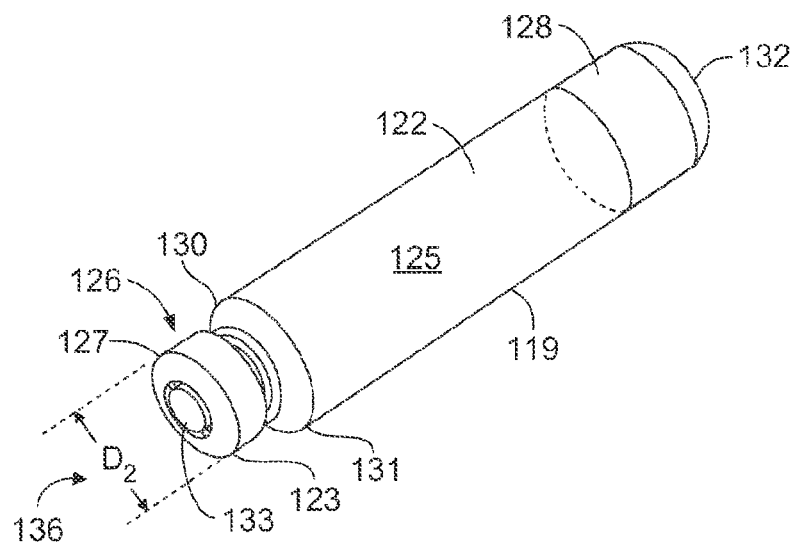
FIG. 1b illustrates an exemplary drug cartridge.

An inner cartridge cavity 111 defined by the cartridge holder 104 is dimensioned and configured to securely receive and retain a cartridge, such as glass cartridge 119. FIG. 1b illustrates a perspective view of the cartridge 119 that may be used with the drug delivery device 100 illustrated in FIG. 1a. Typically, the cartridge 119 is manufactured of glass and includes a generally tubular barrel 122 extending from a distal end 130 to a proximal end 132.

At the distal end 130, the cartridge 119 includes a smaller diameter neck 126 and this neck 126 projects distally from the shoulder 131 of the barrel 122. Preferably, this smaller diameter neck 126 is provided with a large diameter annular bead 123 and this bead 123 extends circumferentially thereabout at the extreme distal end of the neck 126 and defines an opening 127. A pierceable seal or septum 133 is securely held across the opening 127 by a metallic sleeve or a ferrule.

The medicament 125 is pre-filled into the cartridge 119 and is retained within this cartridge 119, in part, by the pierceable seal 133, a ferrule, and the stopper 128. The stopper 128 is in sliding fluid-tight engagement with the inner tubular wall of the barrel 122. Axially directed forces acting upon the stopper 128 during dose injection or dose administration urges the medication 125 from the cartridge 119 through a double ended needle mounted onto the distal end 108 of the cartridge holder 104 and into the injection site. Such axial directed forces may be provided by the spindle 109 working in unison with the dose setting member 102.

A portion of the cartridge holder 104 defining the cartridge holder cavity 111 is of substantially uniform diameter represented in FIG. 1 by diameter D1 134. This diameter D1 134 is preferably slightly greater than the diameter D2 136 of the cartridge 119. The interior of the cartridge holder 104 includes an inwardly-extending annular portion or stop that is dimensioned to prevent the cartridge 119 from moving within the cartridge holder 104. In this manner, when the cartridge 119 is loaded into the cavity 111 of the cartridge holder 104 and the cartridge holder 104 is then connected to the dose setting member 102, the cartridge 119 will be securely held within the cartridge cavity 111.

A number of doses of a medicament 125 may be dispensed from the cartridge 119. Preferably, the cartridge 119 contains a type of medicament 125 that must be administered often, such as one or more times a day. One such medicament 125 is insulin.

The dose setting mechanism 102 comprises a dose setter 117 at the proximal end of the dose setting mechanism 102. In one preferred arrangement, the dose setter 117 is rotated to set a dose. To administer this set dose, the user attaches a needle assembly comprising a double ended needle on the distal end of the cartridge holder 104. In this manner, the needle assembly pierces the seal 133 of the cartridge 119 and is therefore in liquid communication with the medicament 125. The user pushes on the dose setter 117 to inject the set dose. The same dose setting and dose administration procedure is followed until the medicament 125 in the cartridge 119 is expended and then a new cartridge 119 must be loaded in the device 100. To exchange an empty cartridge 119, the user is called upon to remove the cartridge holder 104 from the dose setting mechanism 102.

In accordance with the proposed concepts, a cartridge assembly (e.g., a cartridge holder holding a cartridge, or a molded drug cartridge) may be coded to a drug delivery device such that when a correct coded assembly is attached to the device, dispensing of a dose is allowed. However, when a holder is attached to a drug delivery device that is not correctly coded for that particular holder, dispensing of a dose is prevented. Thus, when an incorrect cartridge assembly is attached to the drug delivery device, dispensing of a drug will not be possible. Preventing dispensing of a drug for an incorrect cartridge assembly and allowing dispensing of a drug for a correct cartridge assembly may be accomplished in a variety of ways. For example, in an embodiment, dispense of a drug may be allowed by preventing rotation of a spindle nut of a drug delivery device, and dispense may be prevented by not preventing rotation of the spindle nut. In another embodiment, preventing dispense of a drug may be accomplished by preventing rotation of the spindle when an incorrect cartridge assembly is inserted. In yet another embodiment, preventing dispense of a drug may be accomplished by preventing axial movement in a distal direction of the spindle when an incorrect cartridge assembly is inserted. These various embodiments will be described in greater detail in the following subsections.

I. Preventing Rotation of the Spindle Nut

In this embodiment, rotation of a spindle nut of a drug delivery device is controlled. When a correct cartridge assembly is attached, the spindle nut is prevented from rotating. Preventing rotation of the spindle allows for the spindle to move axially, and this allows for dispensing of a dose. However, when an incorrect cartridge assembly is attached, the spindle nut is not prevented from rotating, and this prevents dispensing of a drug. Therefore, this embodiment only allows a drug delivery device to dispense a drug for a correct cartridge assembly.

The disclosed concept of enabling dispense of a correct drug by preventing rotation of a spindle nut may be accomplished in several ways. Generally, if coding features on the cartridge assembly do not match coding features of the drug delivery device (e.g., in the dose setting mechanism), dispense of a drug will not be possible. If the spindle nut is free to rotate, the spindle which is attached to the nut preferably via helical threads will not advance axially along the helical threads to dispense the drug.

In accordance with this embodiment, the dose setting mechanism comprises (i) a spindle, (ii) a spindle nut, wherein the spindle nut is engaged with the spindle, and (iii) a coding feature. The coding feature is configured such that the coding feature facilitates preventing dispensing of a drug when an incorrect cartridge assembly is attached to the dose setting mechanism. Specifically, when a correct cartridge assembly is inserted in the dose setting mechanism, the coding feature interacts with a corresponding coding feature of the cartridge holder to prevent the spindle nut from rotating. However, when an incorrect cartridge assembly that does not have the corresponding coding feature is inserted in the dose setting mechanism, the spindle nut remains free to rotate, and this free rotation of the spindle nut prevents axial movement of the spindle.

Example dose setting mechanisms in accordance with this embodiment are described with reference to FIGS. 2-9. In these examples, the dose setting mechanism includes coding features that are configured so that when they interact with corresponding coding features of a cartridge assembly, the coding features allow for dispensing of a dose of medication. However, when an incorrect cartridge assembly is attached to this example dose setting mechanism, dispensing of a drug will be prevented.

Figure 2:
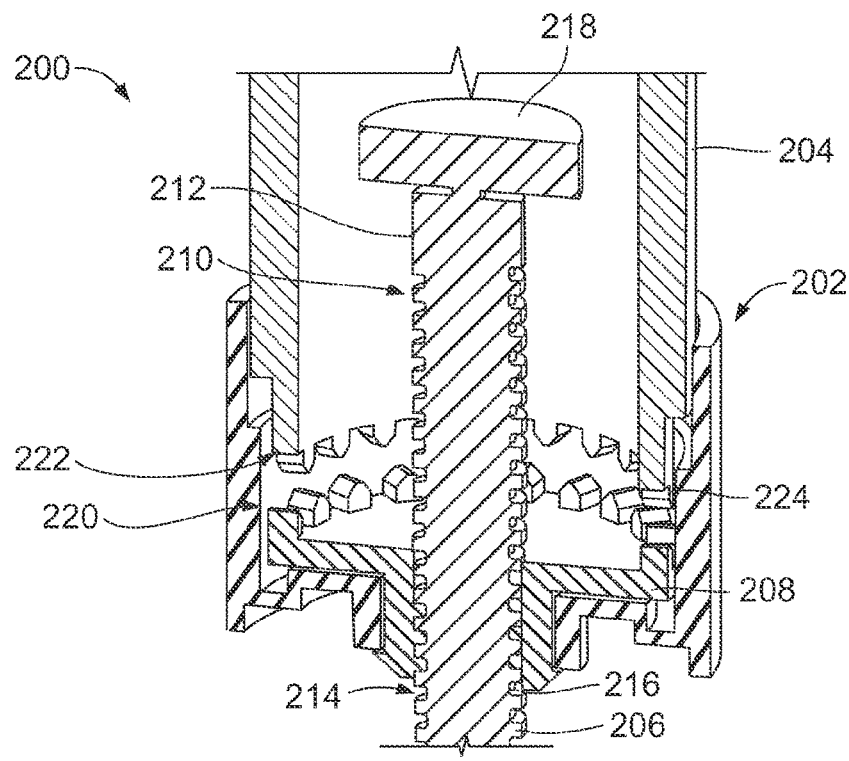
FIG. 2 illustrates a cross-sectional perspective view of a distal portion of an exemplary dose setting mechanism and a proximal portion of an exemplary cartridge assembly.

FIG. 2 depicts drug delivery device 200, which includes dose setting mechanism 202 connected to cartridge assembly 204. The dose setting mechanism 202 includes a spindle 206 and a spindle nut 208. The spindle 206 has a first helical groove 210 extending along the outer surface 212 of the spindle 206. Further, the spindle nut 208 includes a second helical groove 214 extending along the inner surface 216 of the spindle nut 208. Helical groove 210 is engaged with helical groove 214. Thus, the spindle 206 may move axially with respect to the spindle nut 208 when the spindle nut 208 is fixed. Preventing the spindle nut 208 from rotating in the dose setting mechanism 202 therefore allows axial movement of the spindle 206. The axial movement of the spindle 206 allows the spindle 206 to advance forward, and the plunger 218 may provide an axially directed force upon a stopper in a drug cartridge to urge medication from the cartridge through an attached double ended needle mounted on the distal end of cartridge assembly 204. However, when the spindle nut 208 is free to rotate, the spindle 206 is prevented or substantially prevented from applying an axial force on the cartridge, which prevents dispensing of a dose.

Dose setting mechanism 202 also includes coding feature 220. In this example, the coding feature 220 is disposed on the spindle nut 208. In particular, the coding feature 220 is on an upper edge of the spindle nut 208. A coding feature 220 in accordance with embodiments of the proposed system, such as coding feature 220, may take various forms. In this example, coding feature 220 includes a plurality of protrusions disposed along the upper edge of the spindle nut 208. The protrusions are pentagon-shaped protrusions. However, protrusions of any shape (e.g., any polygon-shape) are possible.

The cartridge assembly 204 includes a corresponding coding feature 222. In this example, the corresponding coding feature 222 is disposed on the proximal end 224 of the cartridge assembly 204. Similar to the coding feature 220 of the dose setting mechanism 202, the corresponding coding feature 222 of the cartridge assembly 204 may take various forms. In this example, corresponding coding feature 222 includes a plurality of protrusions (and thus a plurality of indentations). The protrusions are a similar pentagon-shape to the protrusions of the coding feature 220. When the cartridge assembly 204 is inserted into the dose setting mechanism 202, coding feature 220 and corresponding coding feature 222 mesh together. Due to the pentagon-shape with a triangle-shaped top, the coding features 220 and corresponding coding features 222 easily mesh together. When the coding features 220, 222 mesh together, the interaction prevents the spindle nut 208 from rotating.

As mentioned above, the coding feature and corresponding coding features may take various forms. In general, the coding features may take any form now known in the art or later developed. In particular, the coding features may be varied by varying the number of features, size of features, position of features, and the symmetry of the features. A large number of cartridge assemblies and drugs can, therefore, be distinguished from one another.

Beneficially, by preventing rotation of the spindle nut 208, the dose setting mechanism 202 may operate so as to ensure that a user can only dispense the correct drug from a drug delivery device 200. If an incorrect cartridge assembly is inserted, the spindle nut 208 will not be locked, and thus the spindle 206 will not be free to move axially. Therefore, the dose setting mechanism 202 is capable of preventing dispensing of a drug when an incorrect cartridge assembly 204 is connected.

Figure 3:
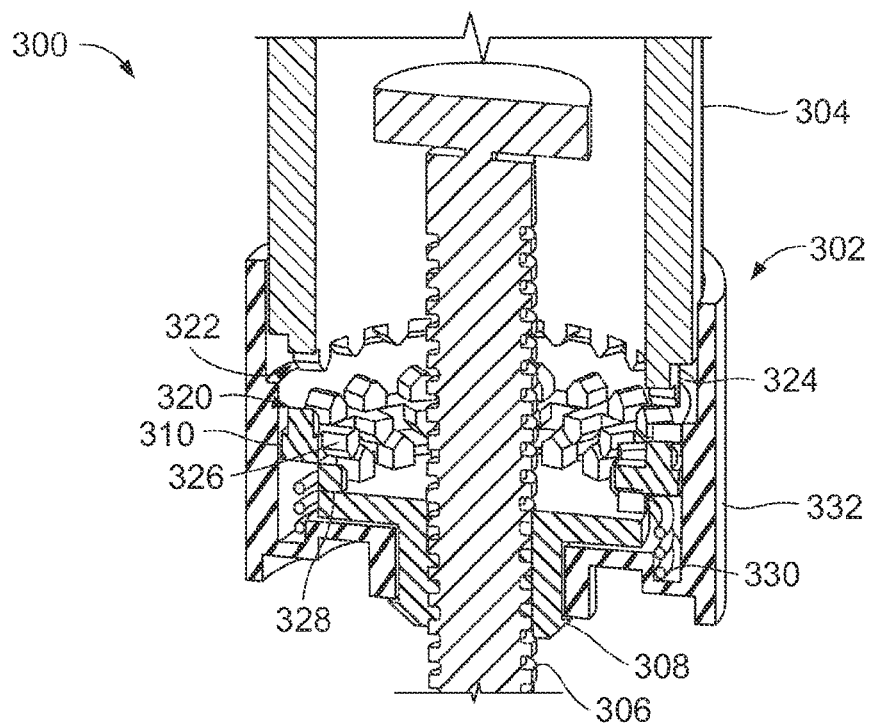
FIG. 3 illustrates a cross-sectional perspective view of a distal portion of an exemplary dose setting mechanism and a proximal portion of an exemplary cartridge assembly.

Another example of a dose setting mechanism that prevents dispensing of a dose when an incorrect cartridge assembly is attached is shown in FIG. 3. FIG. 3 depicts drug delivery device 300, which includes dose setting mechanism 302 connected to cartridge assembly 304. The dosing mechanism of dose setting mechanism 302 includes spindle 306, a spindle nut 308, and a lock nut 310.

Dose setting mechanism 302 also includes coding feature 320. Rather than being disposed on the spindle nut 308 as in FIG. 2, the coding feature 320 is instead disposed on the lock nut 310. Coding feature 320 comprises a plurality of protrusions. Cartridge assembly 304 has a corresponding coding feature 322 located on the proximal end 324 of the cartridge assembly 304. When the cartridge assembly 304 is inserted into the dose setting mechanism 302, coding feature 320 and corresponding coding feature 322 mesh together. These coding features 320, 322 may mesh during the initial fastening action, and thereafter the lock nut 310 and assembly 304 travel together. The lock nut 310 and the cartridge assembly 304 may travel axially or helically to engage with the spindle nut 308. Teeth 326 on the lock nut 310 mesh with teeth 328 on the spindle nut 308, and if fastening of the cartridge assembly 304 includes rotational movement, the lock nut 310 also rotates relative to the body or housing 332 of the dose setting mechanism 302. Once fully assembled, the spindle nut 308 cannot rotate. Since the cartridge assembly 304 is not able to rotate, the locknut 310 is unable to rotate. Further, since the lock nut 310 is unable to rotate and is engaged with the spindle nut 308, the spindle nut 308 is also unable to rotate. If the lock nut 310 did not mesh with the cartridge assembly 304, however, the lock nut 310 would be able to rotate, and thus so would the spindle nut 308.

Dose setting mechanism 302 may also include a spring 330. The spring 330 may bias the lock nut 310 axially when a cartridge assembly 304 is not attached. The spring 330 prevents the lock nut 310 from engaging with the spindle nut 308 when a cartridge assembly 304 is not inserted. Specifically, the spring 330 prevents teeth 326 and teeth 328 from meshing when an assembly 304 is not connected. Without the spring 330, the lock nut 310 can float axially, e.g. due to gravity, and may lock the spindle nut 308 accidentally. Also, biasing in a distal direction ensures that the coding from cartridge to lock nut 310 can mesh before the teeth 326, 328 from lock nut 310 to spindle nut 308.

Figure 4:
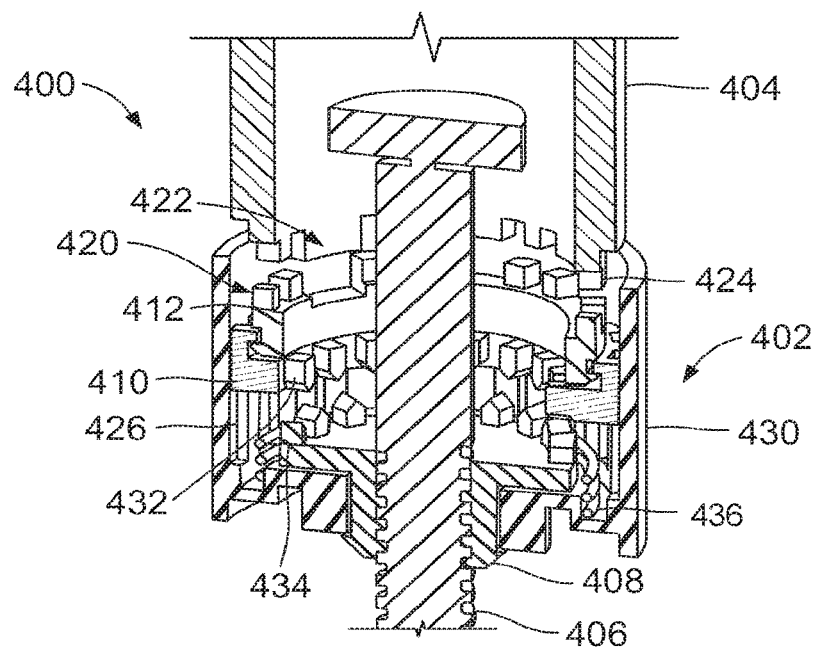
FIG. 4 illustrates a cross-sectional perspective view of a distal portion of an exemplary dose setting mechanism and a proximal portion of an exemplary cartridge assembly.

Another example dose setting mechanism that beneficially ensures that a user can only dispense the correct drug from a drug delivery device is shown in FIG. 4. In this Figure, the cartridge assembly is coded to a collar on the lock nut (this collar may also be referred to as a distal lock nut). FIG. 4 depicts a drug delivery device 400, which includes dose setting mechanism 402 and cartridge assembly 404. The dosing mechanism of dose setting mechanism 402 includes spindle 406, spindle nut 408, a proximal lock nut 410, and a distal lock nut 412.

In some of the examples discussed above, rotation of the cartridge assembly after meshing of the teeth is transferred to the spindle nut, and this rotation may in turn drive the spindle axially and pre-compress the cartridge bung. There may then be a loss of medicament when a needle is attached. Generally, in the example of FIG. 4, the proximal lock nut can move axially but cannot rotate relative to the housing of the dose setting mechanism, whereas the distal lock nut is fixed axially to the proximal lock nut but can rotate. This arrangement beneficially allows the cartridge assembly to be fastened rotationally without significant rotation of the spindle nut.

Dose setting mechanism 402 also includes coding feature 420, which is disposed on the distal lock nut 412. Cartridge assembly 404 has a corresponding coding feature 422 located on proximal end 424 of the cartridge assembly 404. As mentioned above, the coding features 420, 422 may take various forms in order to distinguish various cartridge assemblies 404 and drugs. The coding features 420 and 422 are rectangular-shaped coding features, which differ from the coding features depicted in FIGS. 2 and 3. Further, while the coding features of FIGS. 2 and 3 includes protrusions of the same size, the protrusions of coding features 420 and 422 include a plurality of protrusions having different sizes. Varying the size of protrusions increases the different coding combinations.

The dose setting mechanism 402 also has at least one spline feature, such as splines 426, on inner wall of the housing 430 of the dose setting mechanism. Splines 426 (i) prevent the proximal nut lock nut 410 from rotating while (ii) allowing the proximal lock nut 410 to move axially.

When a correct cartridge assembly 404, such as cartridge assembly 404, is attached to dose setting mechanism 402, the coding features 420 mesh with corresponding coding features 422, and the distal lock nut 412 is free to rotate along with the cartridge assembly 404. During the fastening action, the assembly 404 may then force the proximal nut 410 axially, and teeth 432 may then engage with teeth 434 in order to prevent rotation of spindle nut 408. As mentioned above, this arrangement beneficially allows the cartridge assembly 404 to be fastened rotationally without significant rotation of the spindle nut 408.

Dose setting mechanism 402 may also include a spring 436. The spring 436 biases the lock nut 410 axially when a cartridge assembly 404 is not attached. The spring 436 prevents the lock nut 410 from engaging with the spindle nut 408 when a cartridge assembly 404 is not inserted. Specifically, the spring 436 prevents teeth 432 and teeth 434 from meshing when an assembly 404 is not connected.

Figure 5:
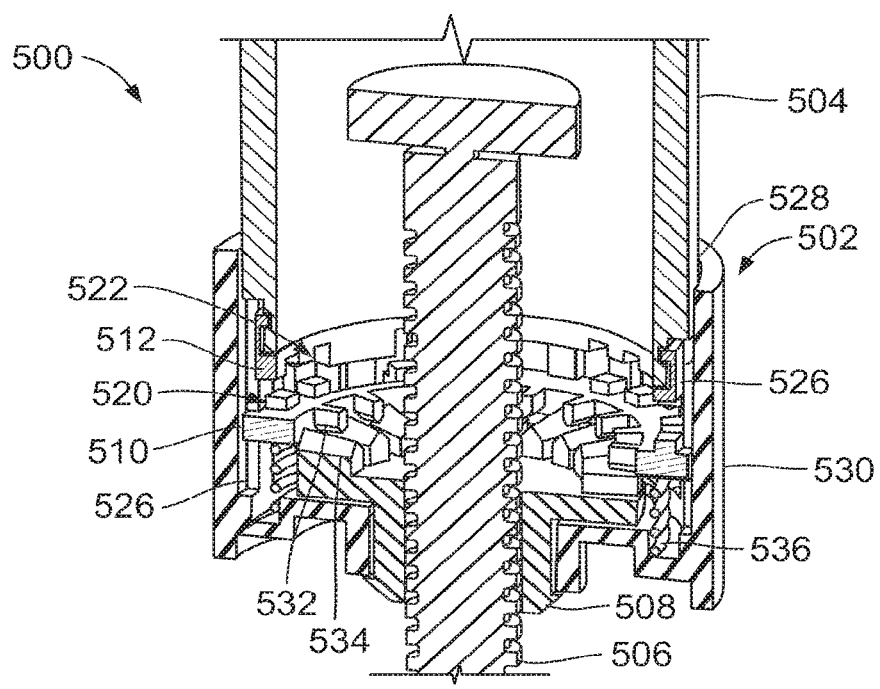
FIG. 5 illustrates a cross-sectional perspective view of a distal portion of an exemplary dose setting mechanism and a proximal portion of an exemplary cartridge assembly.

Another example dose setting mechanism that beneficially ensures that a user can only dispense the correct drug from a drug delivery device is shown in FIG. 5. This example is similar to the example depicted in FIG. 4. Generally, a collar on the proximal end of the cartridge assembly is fixed axially relative to the cartridge assembly, but allows relative rotation. Coding features on the collar mesh with the lock nut, which can move axially but cannot rotate relative to the body.

Specifically, FIG. 5 depicts a drug delivery device 500, which includes dose setting mechanism 502 and cartridge assembly 504. The dose setting mechanism 502 includes spindle 506, spindle nut 508, and lock nut 510. The dose setting mechanism 502 also includes coding feature 520 disposed on the lock nut 510. The cartridge assembly 504 includes a collar 512 that is attached to the proximal end. The collar 512 has a corresponding coding feature 522.

The dose setting mechanism 502 also has at least one spline feature, such as splines 526, on inner wall 528 of the housing 530 of the dose setting mechanism 502. Splines 526 (i) prevent the nut lock nut 510 from rotating while (ii) allowing the lock nut 510 to move axially.

When the cartridge assembly 504 is inserted into the dose setting mechanism 502, coding feature 520 and corresponding coding feature 522 mesh together. Next, teeth 532 on the lock nut 510 mesh with teeth 534 on the spindle nut 508. Once fully assembled, the spindle nut 508 cannot rotate.

Dose setting mechanism 502 may also include a spring 536. The spring 536 biases the lock nut 510 axially when a cartridge assembly 504 is not attached. The spring 536 prevents the lock nut 510 from engaging with the spindle nut 508 when a cartridge assembly 504 is not inserted. Specifically, the spring 536 prevents teeth 532 and teeth 534 from meshing when an assembly 504 is not connected.

It should be understood that, in the examples discussed above, the coding means between the cartridge assembly, collar, lock nut, and/or spindle nut may be achieved using various coding features. As described above, coding features may be varied by varying the number of features, size of features, position of features, and/or symmetry of features. This allows for many cartridge assemblies and therefore many drugs to be distinguished from one another. Further, the coding system beneficially allows for compact coding features.

In some of the examples discussed above, the cartridge assembly may rotate after meshing of the coding feature and corresponding coding feature. This rotation may also rotate the spindle nut, and hence lead to some travel of the spindle. Therefore, the thread on the fastening means for connecting the cartridge assembly to the dose setting mechanism may be the opposite hand to the spindle thread. If the thread on the fastening means for connecting the cartridge assembly to the dose setting mechanism is the opposite hand to the spindle thread, the spindle would retract away from the cartridge. This retraction would beneficially reduce the risk of pre-compressing the bung.

In the examples above, the coding features are preferably aligned at the start of the fastening action. Alignment of the coding features at the start of the fastening action may be achieved in various ways. For example, the coding can be repeated around the circumference of the element that the coding feature is disposed on (e.g., spindle nut, lock nut, distal lock nut). Every feature of the coding feature may contain all the necessary coding, e.g., by pitch, height, or shape of the feature. Alternatively, coding might be repeated the same as the fastening means, e.g., if the holder can be fastened in two orientations, the coding would be included twice as well.

Alignment features on each coded part could ensure that the fastening means is aligned with the coding. For example, long features on each part could engage and align the parts before the start of the fastening operation.

Further, when the cartridge assembly is unfastened, a detent could keep the coding in the correct orientation for the next fastening operation. For example, in FIG. 3, at the start of the fastening operation, the coding on the lock nut 310 should be aligned with coding on cartridge. When assembled to a correct cartridge the coding is aligned, but if the lock nut is free to rotate, it may move out of alignment when the cartridge is not in place. To keep the lock nut in alignment when disassembled, a detent may hold the lock nut in the correct circumferential position until the next cartridge is assembled.

In the examples where one of the coded components is able to rotate relative to the housing, it could be constrained to follow the fastening action, e.g., with a pin and groove parallel to those for the fastening means. When the cartridge assembly is unfastened, the coded component would be biased in the distal direction by the spring and be retained in the correct orientation for the next fastening operation. For example in FIG. 3, the cartridge fastening may comprise a pin/groove that may unfasten first rotationally, then helically, then axially. The lock nut 310 may also follow this path because it is meshed to the cartridge by the coding, but may also have its own pin/groove following the same path. The spring would help force the lock nut out along the path, and would help keep the lock nut in the axial section after the cartridge is removed, so it is in the correct position next time a cartridge is fitted.

Figure 6:
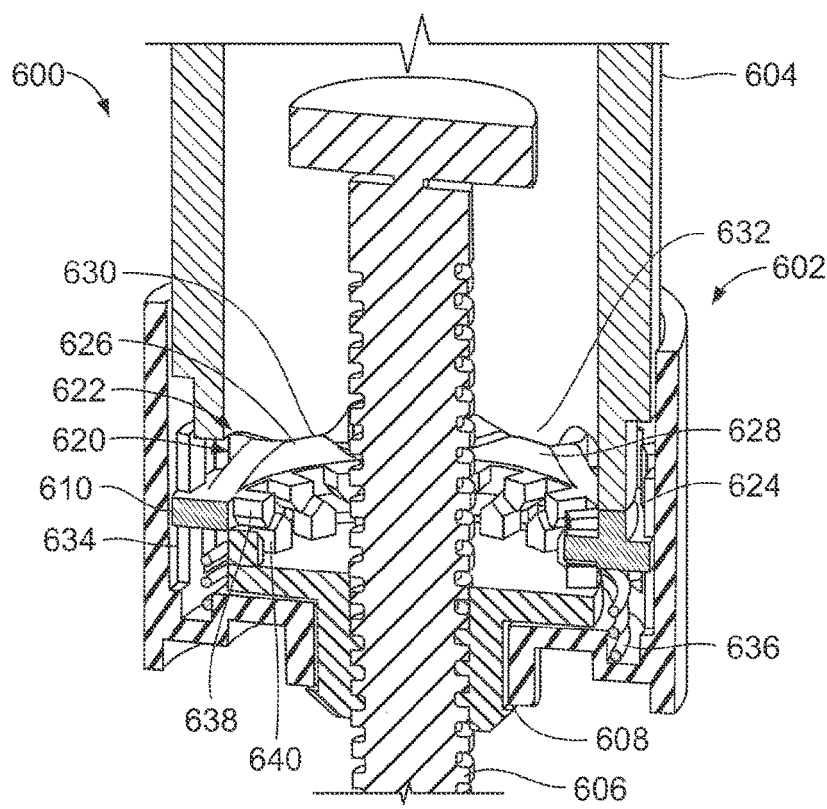
FIG. 6 illustrates a cross-sectional perspective view of a distal portion of an exemplary dose setting mechanism and a proximal portion of an exemplary cartridge assembly.

Another example dose setting mechanism that beneficially ensures that a user can only dispense the correct drug from a drug delivery device is shown in FIG. 6. In this example, the coding features are cam features. Generally, as the cartridge assembly rotates, cams on the proximal end interact with cams on a locknut and drive the locknut axially to mesh with the spindle nut and prevent rotation of the spindle nut. However, if the cam features on both parts do not match, dispense will not be possible, or it will not be possible to attach the cartridge to the device.

FIG. 6 depicts a drug delivery device 600, which includes dose setting mechanism 602 and cartridge assembly 604. The dose setting mechanism 602 includes spindle 606, spindle nut 608, and lock nut 610. The dose setting mechanism 602 also includes coding feature 620 disposed on the lock nut 610.

The cartridge assembly 604 includes a corresponding coding feature 622 disposed on the proximal end 624. In this example, the coding features 620 and corresponding coding features 622 comprise a plurality of cam features. In particular, coding feature 620 includes cam features 626, 628, and corresponding coding feature 622 includes cam features 630, 632. Further, the dose setting mechanism 602 includes splines 634 on the inner wall of the housing. The lock nut 610 may engage with the splines 634, so that the lock nut 610 is constrained rotationally but may move axially. Additionally, dose setting mechanism 602 may include a spring, such as spring 636. The spring 636 may beneficially prevent teeth 638 and 640 from meshing with one another when a cartridge assembly 604 is not inserted.

In the example of FIG. 6, the cams can activate the lock nut during the rotational part of the fastening operation (i.e., after the cartridge has been fully inserted into the device). This beneficially minimizes pre-loading of the bung, which might occur if the spindle nut 608 is locked too early. When cam features 626, 628 interact with cam features 630, 632, the interaction of the cams forces the lock nut 610 down axially, which thereafter forces teeth 638 to mesh with teeth 640. This prevents rotation of the spindle nut 608.

Figure 7A:
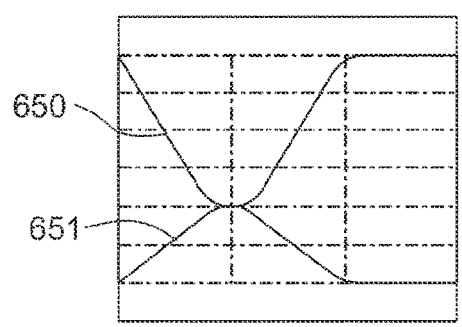
FIGS. 7a-b illustrate possible examples of cams of the dose setting mechanism and cartridge assembly of FIG. 6.
Figure 7B:
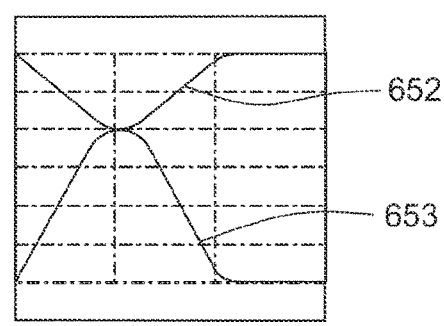

In accordance with this embodiment, coding of different cartridge assemblies and therefore different drugs may be achieved in various ways. For example, the number of cam features may be varied. As another example, the size of the cam features may be varied for various drugs. For instance, the axial, circumferential, and/or radial extent of the features may be varied. In a preferred embodiment, the axial extents of the cam features are varied. As an example, cams having different axial extents are depicted in FIGS. 7a and 7b, shown as a projection around the circumference. FIG. 7a shows a cam arrangement to be used with a first drug, comprising a cam 650 of a cartridge assembly and a cam 651 of a dose setting mechanism. If cam 650 did not have such a large axial extent, cam 650 would be unable to interact with cam feature 651 when the cartridge assembly is attached to the dose setting mechanism. FIG. 7b shows a cam arrangement for a second drug, comprising a cam 652 of a cartridge assembly and cam 653 of a dose setting mechanism. In comparison to FIG. 7a, the cam feature 652 of the cartridge assembly has a smaller axial extent than the cam feature 650, while cam feature 653 has a larger axial extent than cam feature 651.

As yet another example of different coding, the position of the cam features may be varied for various drugs. For instance, the axial, circumferential, and/or radial position may be varied, especially relative to a standard feature. Particular examples include varying the circumferential position relative to the fastening means, or radial position.

Beneficially, if the cartridge assembly fits in only one orientation, the number of coding combinations is increased. Alternatively, the coding may be included more than once, offering redundancy of coding. Redundant sets of coding may be beneficial, for instance, in case one set of the coding is damaged. Further, this redundant coding may also allow the user to insert the cartridge assembly in more than one orientation.

Figure 8A:
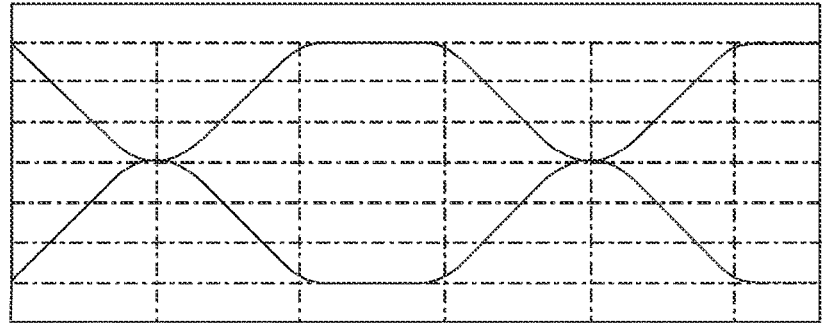
FIGS. 8a-c illustrate possible examples of cams of the dose setting mechanism and cartridge assembly of FIG. 6.
Figure 8B:
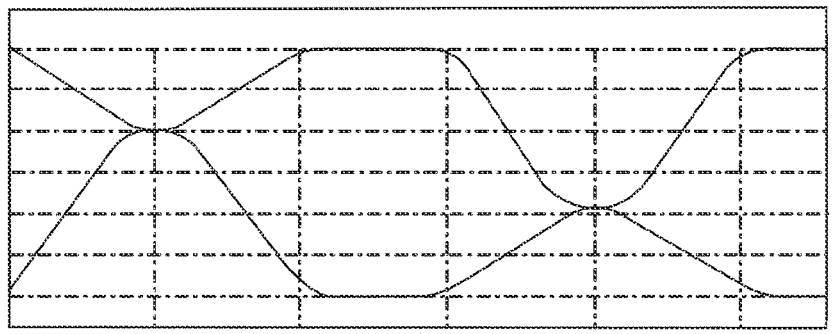
Figure 8C:
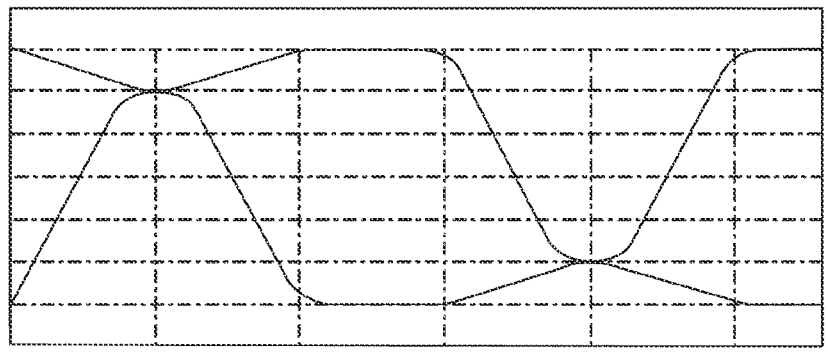

As still yet another example of different coding, the coding may depend on more than one coding feature. A coding system may include a number of cam features, where the cams for each drug are different sizes depending upon the particular drug contained in the cartridge. With only one feature, only two combinations are possible (see FIGS. 7a-b). However, by combining two features, more combinations are possible. For instance, three examples of coding for two cam features are shown in FIGS. 8a-c as projections around the circumference. The lower cams are on the cartridge assembly and the upper cams are on the dose setting mechanism. Each example shows the cam arrangement intended for a different drug. In these examples, the cams on the cartridge assembly for one drug cover an area that is not covered completely by the cams for any of the other drugs, so that if a cartridge assembly is connected to an incorrect dose setting mechanism, the cams would interfere and prevent assembly. In alternative arrangements, the cams for one drug may cover an area that is covered by all of the other drugs. In this case, if a holder is connected to an incorrect dose setting mechanism, the cams would not contact and hence the spindle nut would not be locked and dispense would not be possible. Other examples are possible as well. Additional cam features are possible, which would further increase the number of different combinations.

Figure 9:
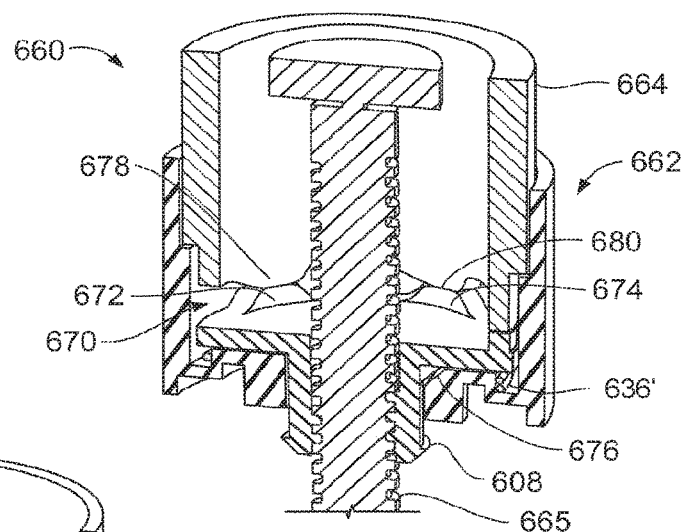
FIG. 9 illustrates a cross-sectional perspective view of a distal portion of an exemplary dose setting mechanism and a proximal portion of an exemplary cartridge assembly.

Another example of a dose setting mechanism having cams as the coding feature is shown in FIG. 9. FIG. 9 depicts a drug delivery device 660, which includes dose setting mechanism 662 and cartridge assembly 664. The dose setting mechanism 662 includes spindle 665 and spindle nut 668. Coding feature 670 including cams 672 and 674 is disposed on the spindle nut 668. The spindle nut 668 further includes at least one tooth, such as tooth 676.

In this example of FIG. 9, there is no lock nut, and cams 678, 680 on the cartridge assembly 664 engage directly with cams 672, 674 on the spindle nut 668. Rotation of the spindle nut 668 is prevented by at least one tooth 676, which engages with a portion of the body (such as, for example, at least one corresponding tooth on the body) of the dose setting mechanism 662 as the cams 672, 674 push the spindle nut 668 axially.

The dose setting mechanism 662 preferably includes a spring 636' that biases the spindle nut 668 to prevent the at least one tooth 676 from engaging with the body of the dose setting mechanism 662 when a cartridge assembly 664 is not inserted in the dose setting mechanism 662.

In some embodiments of the system for preventing or allowing dispensing of a drug by controlling rotation of the spindle nut, an incorrect cartridge is rejected by a spring. In certain of the examples that have a spring loaded lock nut, if the coding is incorrect, the cartridge assembly may not be fully fastened to the device. In this position, the spring forces the lock nut and also the cartridge assembly in a distal direction, hence rejecting an incorrect cartridge.

Beneficially, the system disclosed allows compact coding features. Many different drugs can be distinguished by varying the coding features on the dose setting mechanism and the corresponding coding features on the cartridge assembly.

II. Preventing Rotation of the Spindle

Figure 10A:
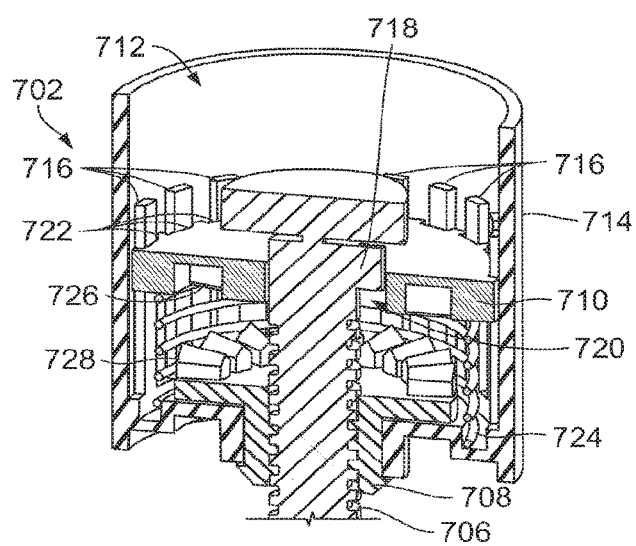
FIG. 10a illustrates a cross-sectional perspective view of a distal portion of an exemplary dose setting mechanism.
Figure 10B:
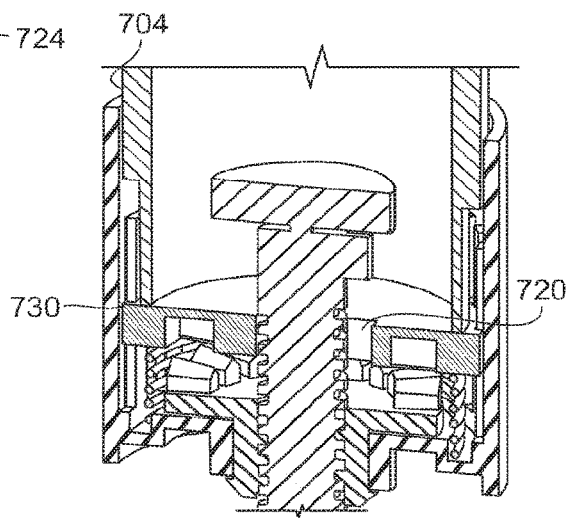
FIG. 10b illustrates a cross-sectional perspective view of the distal portion of the exemplary dose setting mechanism of FIG. 10a attached to a proximal portion of an exemplary cartridge assembly.

Yet another example dose setting mechanism that beneficially ensures that a user can only dispense the correct drug from a drug delivery device is shown in FIGS. 10a-b. However, in this embodiment, rather than coding features interacting to thereafter prevent rotation of the spindle nut, a disc is splined to the spindle and the body of the dose setting mechanism in order to prevent relative rotation of the spindle when a cartridge assembly is not inserted or when an incorrect cartridge assembly is inserted. When a correct cartridge assembly is fastened to the dose setting mechanism, the assembly displaces the disc in the proximal direction and disengages it from the spindle, allowing the spindle to rotate.

FIG. 10a depicts a dose setting mechanism 702 and FIG. 10b depicts the dose setting mechanism 702 attached to a correct cartridge assembly 704. The dose setting mechanism 702 includes spindle 706, spindle nut 708, and locking disc 710. The inner edge 712 of main body 714 includes at least one main-body spline feature, such as spline features 716. Further, the spindle 706 has at least one spindle spline feature, such as spindle spline feature 718. The spindle spline feature 718 is disposed on an outer edge of the spindle 706.

The locking disc 710 includes (i) at least one indentation, such as indentation 720, disposed on the inner edge of the locking disc 710 and (ii) at least one indentation, such as indentations 722, disposed on an outer edge of the locking disc 710. The indentation 720 is configured to engage with the spindle spline feature 718, and the indentations 722 are configured to engage with the main-body spline features 716.

Prior to a cartridge assembly 704 being inserted in the dose setting mechanism 702, the locking disc 710 is engaged with the spindle 706. Such engagement is depicted in FIG. 10a. Further, dose setting mechanism 702 may include a spring 724 to bias the locking disc 710 to engage with the spindle spline feature 718 when a cartridge assembly 704 is not inserted.

FIG. 10b depicts when a correct cartridge assembly 704, such as cartridge assembly 704, is inserted into the dose setting mechanism 702. The cartridge assembly 704 forces the locking disc 710 to disengage from the spindle spline feature 718, thereby allowing the spindle 706 to rotate.

Further, the locking disc 710 may include indentations 726 that mesh with teeth 728 on the spindle nut 708. When these mesh, the locking disc 710 may prevent rotation of the spindle nut 708. Dispense of a drug is therefore possible when a correct cartridge assembly 704 is inserted.

In this example, coding features on the proximal end of the cartridge assembly can unlock the spindle. The coding may, for example, be due to the end face of the cartridge assembly. For instance, cartridge assembly 704 includes an end face 730 that acts to unlock the locking disc 710. However, if a cartridge assembly 704 has an end face 730 with a smaller axial extent than end face 730, the cartridge assembly 704 may be unable to unlock the locking disc 710 from the spindle 706 by displacing the locking disc 710 axially. Other coding may include various size or position of coding features.

A split nut could also lock into the spindle thread, where the nut may move in a traverse direction, or on a ramped surface. The split nut might look like the split ring shown in FIG. 12a, but instead of moving to block axial travel of the plunger, it would move inwards, and splines on its inner face would lock into splines on the outer edge of the spindle.

Further, instead of disengaging from the spline on the spindle, the disc may disengage from the splines on the main body when a correct cartridge assembly is inserted. In such a case, the disc would then follow any rotation of the spindle. However, the spindle would be free to rotate and thus dispense would be possible.

III. Preventing Axial Movement of the Dispensing Mechanism

Additional example dose setting mechanisms that beneficially ensure that a user can only dispense the correct drug from a drug delivery device are shown in FIGS. 11 and 12. Generally, the dose setting mechanism includes a spindle having a plunger feature disposed on the distal end of the spindle, and which may be able to rotate relative to the spindle. The dose setting mechanism also includes a dispensing lock feature, and this dispensing lock feature is capable of a locked and unlocked position. When a correct cartridge assembly is inserted into the dose setting mechanism, the dispensing lock feature is forced into the unlocked position, thereby allowing the plunger to pass beyond the dispensing lock feature. However, when an incorrect cartridge assembly is inserted into the dose setting mechanism, the dispensing lock feature remains in the locked position. The dispensing lock feature in the locked position prevents the plunger from advancing beyond the dispensing lock, thereby preventing dispensing of a dose.

In the example of FIG. 11, the dosing mechanism is preferably fully reset before an assembly is attached, and in this reset position, inwardly directed arms on a dispensing lock prevent advancement of the plunger of the spindle. Once the correct cartridge assembly has been attached, the arms are opened, and the open arms allow the plunger to pass through.

Figure 11A:
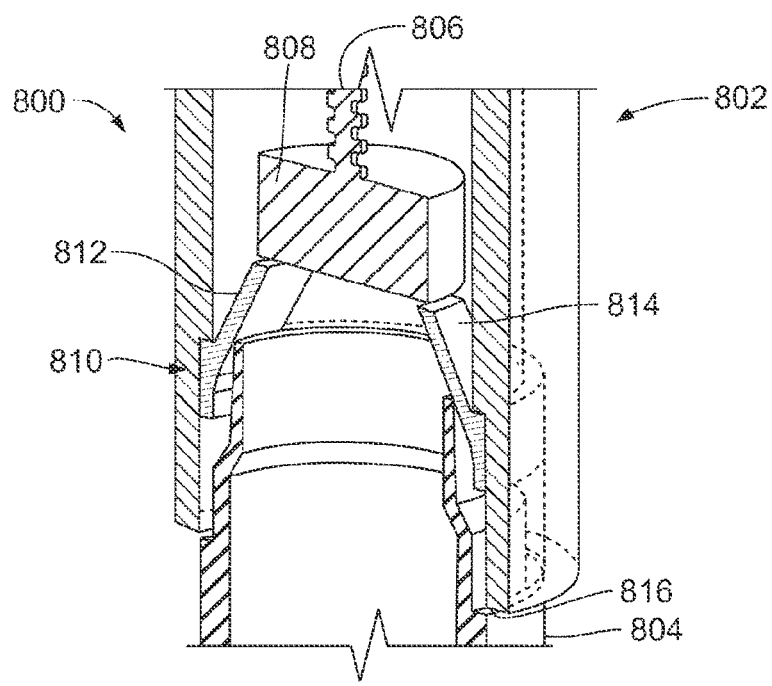
FIG. 11a illustrates a cross-sectional perspective view of a distal portion of an exemplary dose setting mechanism and a proximal portion of an exemplary cartridge assembly.
Figure 11B:
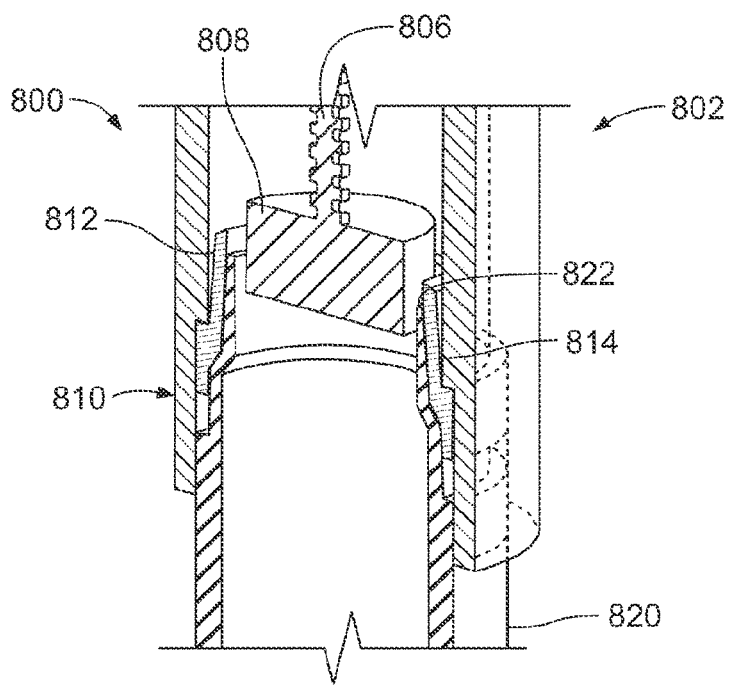
FIG. 11b illustrates a cross-sectional perspective view of a distal portion of an exemplary dose setting mechanism and a proximal portion of an exemplary cartridge assembly.

Specifically, FIG. 11a depicts when an incorrect cartridge assembly 804 and dose setting mechanism 802 are attached, and FIG. 11b depicts when a correct cartridge assembly 820 and dose setting mechanism 802 are attached.

The dose setting mechanism 802 includes a spindle 806, and the spindle 806 includes a plunger 808 disposed on the distal end. In an embodiment, the dispensing lock feature 810 includes at least one arm. For instance, the dispensing lock feature 810 includes arms 812 and 814. Additional arms or fewer arms are possible. Additional arms may beneficially increase the strength of the dispensing lock feature 810. For instance, the lock feature 810 may include six arms around the circumference of the lock feature 810. In FIG. 11a, the arms 812, 814 are in the locked position. In the locked position, the arms 812, 814 are directed inwards as shown in FIG. 11a. Further, the dispensing lock feature 810 may be disposed on an inner wall of the dose setting mechanism 802.

When the incorrect cartridge assembly 804 is inserted, the arms 812, 814 remain in the locked position. In the example of FIG. 11a, the incorrect cartridge assembly 804 is unable to move the dispensing lock feature 810 in the unlocked position because the assembly 804 is prevented from moving further axially by the dose setting mechanism 802 at point 816.

When a correct cartridge assembly 820 is inserted into the dose setting mechanism 802, however, the dispensing lock feature 810 moves into an unlocked position. As seen in FIG. 11b, when the arms 812, 814 are in the unlocked position, the plunger 808 may pass through the dispensing lock feature 810. Thus, dispensing is possible. In the unlocked position, the at least one arm 812, 814 may be positioned in a direction generally parallel to an outer housing of the drug delivery device 800. However, the arms 812, 814 may be angled in the unlocked position, so long as the diameter of the opening of the arms 812, 814 is greater than the diameter of the plunger 808.

A correct cartridge assembly 820 for dose setting mechanism 802 is preferably coded so that it may unlock the dispensing lock feature 810 as the cartridge assembly 820 is attached. Coding features on the proximal end of the cartridge assembly 820 can unlock the dispensing lock feature 810. Coding may, for example, be due to the position of the end face of the cartridge assembly 820. For instance, the end face 822 of cartridge assembly 820 is long enough so that when the assembly 820 is attached, the assembly 820 moves the lock arms 812, 814 to the unlocked position. Other coding is possible, such as size and position of coding elements.

In the embodiment depicted in FIG. 11a, the dose setting mechanism is able to prevent dispense if the dispensing lock mechanism is in the locked position. Thus, after the dispensing lock mechanism has moved into the unlocked position, the dispensing lock mechanism will need to be reset before inserting another cartridge assembly. When a cartridge has been finished, the plunger has advanced past the dispensing lock mechanism which unlocks the spindle. If an incorrect cartridge is inserted without fully resetting the plunger to the proximal side of the lock, the mechanism may remain unlocked, and thus it would be possible to dispense from the incorrect cartridge. To prevent this, an additional mechanism (not shown) could ensure that a cartridge assembly can only be inserted after the dispensing lock feature is fully reset.

The dispensing mechanism of this embodiment for preventing axial travel of the spindle may be of any type. In the example depicted, the dispensing mechanism is a spindle that rotates during dispense and can be reset after dispense. Another example dispensing mechanism may be a rack and pinion. Other examples are possible as well.

Figure 12A:
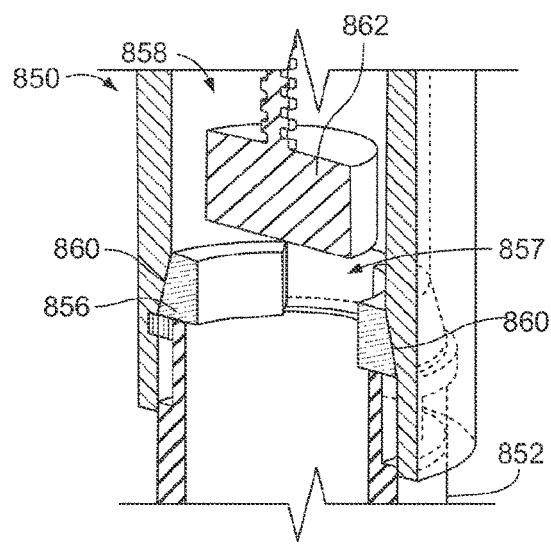
FIG. 12a illustrates a cross-sectional perspective view of a distal portion of an exemplary dose setting mechanism and a proximal portion of an exemplary cartridge assembly.

The dispensing lock feature may take other forms as well. For example, the dispensing lock feature may be a split ring. With an incorrect cartridge assembly, the ring may be pushed into the body against an angled surface, decreasing the internal diameter of the split ring so that it is less than that of the plunger. When the internal diameter of the split ring is less than that of the plunger, the dose setting mechanism is prevented from dispensing. FIG. 12a shows a dose setting mechanism 850 with a correct cartridge assembly 852 attached, and FIG. 12b shows the dose setting mechanism 850 with an incorrect cartridge assembly 854 attached.

The split ring 856 is disposed on an inner wall 858 of the dose setting mechanism 850. The split ring 856 may be a generally circular ring shaped object comprising a split, such as split 857. Accordingly, the diameter of the split ring 856 may be changed depending on how compressed the split ring 856 is. The inner wall 858 comprises an angled surface 860, and the outer edge of the split ring 856 has a similarly angled feature. When the correct cartridge assembly 852 is inserted, the internal diameter of the split ring 856 remains greater than the diameter of the plunger 862. However, when an incorrect cartridge assembly 854, such as assembly 854 in FIG. 12b, is inserted, the split ring 856 may travel along the angled surface 860, compressing the split ring 856. The diameter of the split ring 856 is compressed to a diameter smaller than that of the plunger 862.

Figure 12B:
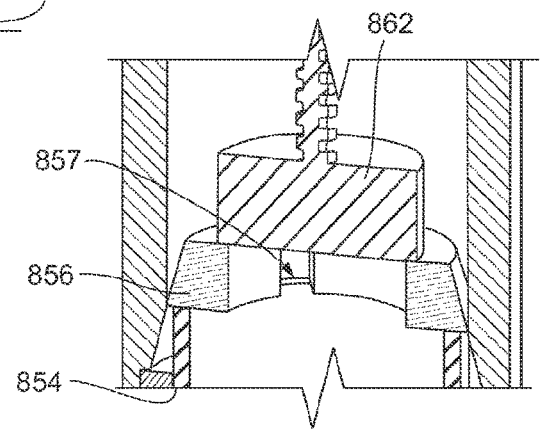
FIG. 12b illustrates a cross-sectional perspective view of a distal portion of an exemplary dose setting mechanism and a proximal portion of an exemplary cartridge assembly.

Although in the example depicted in FIG. 12b, the entire split ring 856 is located above the angled surface 860, this is not necessary. The split ring 856 may be in the locked position when at least a portion of the split ring 856 is above the angled surface 860, as long as the diameter of the split ring 856 is compressed to a smaller diameter of the plunger 862. Other ways of compressing the diameter of the split ring 856 may be possible as well.

Although aimed primarily at the insulin market, the presently proposed system may apply to other drugs. The presently proposed system may apply to various devices, including the following examples:

a. An injector pen with a cartridge (e.g. 3 ml cylindrical glass cartridge) and a separate holder.

b. An injector pen with a cartridge (e.g. 3 ml cylindrical glass cartridge) non removably retained in a holder, so that the holder will be disposed of with the primary pack.

c. An injector pen where the primary pack attaches directly to the pen, e.g. an injection moulded polymer cartridge.

Figure 13:
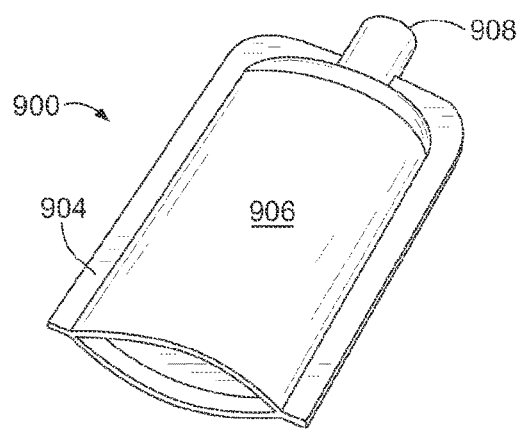
FIG. 13 is a perspective view of an exemplary drug reservoir that may be coded in accordance with the proposed concept.

In other situations, the proposed coding system may apply to any drug delivery device, with any type of reservoir or primary pack, e.g. inhaler, pouch. For example, FIG. 13 illustrates a drug reservoir 900 comprising a vessel 904 that contains a medicament 906. A stopper is provided along a distal end of the vessel 904 and is attached to the vessel 904 so as to prevent the medicament 906 from exiting the vessel 904. The coding described above may be provided on the output port 908 of the vessel 904.

Further, although the fastening means to attach the cartridge assembly is preferably a pin following a groove, and travel is preferably axial then helical then rotational, the coding in accordance with the proposed concept may be used with any fastening means and any combination of directions in the travel, including purely axial travel.

The proposed system for preventing dispensing of a dose results in a number of advantages. For example, the proposed cartridge holder and dose setting mechanism assist a user to distinguish between medicaments, thereby helping to ensure that a delivery device can only be used with a medicament for which the device is intended. Therefore, with the coded dose setting mechanism that requires a correct cartridge assembly in order to allow dispensing of a dose, the cartridge assembly is prevented from being confused with any other drug by loading a cartridge assembly with an incorrect or unwanted interface. The disclosed system prevents a user from dispensing a drug when an incorrect cartridge assembly is attached to the dose setting mechanism.

The disclosed system also results in a low cost coding mechanism since the proposed holders and dose setting mechanism do not require a large number of parts and can be manufactured in a cost effective manner. Moreover, there are quite a large number of different coding configurations between the holder and the dose setting mechanism that may be used. Consequently, with proposed schemes of preventing dispense of a dose, a large number of medicaments can be distinguished from one another.

Exemplary embodiments of the present invention have been described. However, as those of skill in the art will recognize certain changes or modifications to such arrangements may be made. Those skilled in the art will understand, however, that further changes, modifications, revisions and/ or additions may be made to the presently disclosed arrangements without departing from the true scope and spirit of the present invention, which is defined by the claims.

The invention claimed is:

1. A dose setting mechanism comprising:
   a spindle;
   a spindle nut engaged with the spindle, wherein the spindle has a first helical groove extending along an outer surface of the spindle, the spindle nut has a second helical groove extending along an inner surface of the spindle nut, and the first helical groove is engaged with the second helical groove; and a lock nut having a first coding feature, wherein the spindle nut comprises one of a first plurality of protrusions and teeth that is configured to non-rotationally engage with one of a second plurality of protrusions and teeth on the lock nut and thereby prevent the spindle nut from rotation relative to the lock nut, wherein when a first cartridge assembly having a second coding feature is inserted in the dose setting mechanism, the first coding feature non-rotationally engages the second coding feature such that the lock nut prevents rotation of the spindle nut and dispensing of a dose is allowed, and wherein when a second cartridge assembly that does not have the second coding feature is inserted in the dose setting mechanism, the spindle nut is allowed to rotate and dispensing a dose is prevented, wherein the first coding feature corresponds to the second coding feature such that, when the first coding feature engages the second coding feature, the lock nut is non-rotationally engaged to the first cartridge assembly wherein the lock nut is allowed to rotate relative to the housing when the second cartridge assembly is inserted in the drive setting mechanism, and wherein the lock nut is prevented from rotating relative to the housing, by the non-rotational engagement between the first coding feature and the second coding feature, when the first cartridge assembly is inserted in the dose setting mechanism.

2. The dose setting mechanism of claim 1, wherein the first coding feature comprises a third plurality of protrusions and wherein the second coding features comprise a fourth plurality of corresponding protrusions, which mesh with the third plurality of protrusions.

3. The dose setting mechanism of claim 1, further comprising a spring in communication with the lock nut, wherein the spring prevents the lock nut from engaging with the spindle nut when the first cartridge assembly is not inserted.

4. The dose setting mechanism of claim 1, wherein the coding feature comprises at least one cam feature, and the corresponding coding feature comprises at least one corresponding cam feature.

5. The dose setting mechanism of claim 4,
wherein the at least one cam feature is disposed on the lock nut,
wherein the interaction of the cam features drives the lock nut axially to mesh with the spindle nut and prevent rotation of the spindle nut.

6. The dose setting mechanism of claim 4, wherein the at least one cam feature comprises a first cam feature and a second cam feature, wherein the first and second cam are different sizes to indicate the particular drug contained in the cartridge.

7. A drug delivery device comprising the dose setting mechanism according to claim 1.

8. A dose setting mechanism comprising:
a spindle,
a spindle nut engaged with the spindle, wherein the spindle has a first helical groove extending along an outer surface of the spindle, the spindle nut has a second helical groove extending along an inner surface of the spindle nut, and the first helical groove is engaged with the second helical groove,
a distal lock nut having a first coding feature located on the distal lock nut;
a proximal lock nut, wherein the distal lock nut is fixed axially to the proximal lock nut; and
at least one spline disposed on an inner wall of a housing of the dose setting mechanism, wherein the at least one spline prevents the proximal lock nut from rotating and allows the proximal lock nut to move axially between a first position and a second position,
wherein the spline prevents the proximal lock nut from rotation relative to the housing in both the first position and the second position,
wherein the spindle-nut is allowed to rotate when the proximal nut is in the first position to thereby prevent dispensing a dose,
wherein the spindle nut is prevented from rotation by the proximal nut when the proximal nut is in the second position to thereby allow dispensing the dose,
wherein when a first cartridge assembly having a corresponding second coding feature is inserted in the dose setting mechanism, (i) the second coding feature engages the first coding feature, (ii) the distal lock nut moves the proximal lock nut from the first position to the second position, (iii) the spline prevents the proximal lock nut from rotation, and (iv) the proximal lock nut non-rotationally engages the spindle nut to thereby allow for dispensing of the dose, and
wherein when a second cartridge assembly that does not have the second coding feature is inserted in the dose setting mechanism, the spindle nut is allowed to rotate to thereby prevent delivery of the dose.

9. The dose setting mechanism of claim 8, further comprising a spring, wherein the spring prevents the proximal lock nut from engaging with the spindle nut when the first cartridge assembly is not inserted.

10. The dose setting mechanism of claim 8, wherein the first coding feature is configured to non-rotationally engage the second coding feature such that insertion of the first cartridge assembly causes the distal locking nut to rotate relative to the proximal locking nut as the distal locking nut moves the proximal locking nut from the first position to the second position.

11. The dose setting mechanism of claim 8, wherein the first coding feature comprises a first plurality of protrusions and wherein the second coding features comprise a second plurality of corresponding protrusions, which mesh with the first plurality of protrusions.

12. The dose setting mechanism of claim 8, wherein the proximal locking nut and the distal locking nut are not threadedly engaged with the spindle.

13. A drug delivery device comprising the dose setting mechanism according to claim 8.

* * * * *